(12) United States Patent
Brown (10) Patent No.: US 7,305,348 B1
(45) Date of Patent: Dec. 4, 2007

(54) AGGREGATING AND POOLING HEALTH RELATED INFORMATION IN A COMMUNICATION SYSTEM WITH FEEDBACK

(75) Inventor: Stephen J. Brown, San Mateo, CA (US)

(73) Assignee: Health Hero Network, Inc., Palo Alto, CA (US)

( * ) Notice: Subject to any disclaimer, the term of this patent is extended or adjusted under 35 U.S.C. 154(b) by 1114 days.

(21) Appl. No.: 09/625,080

(22) Filed: Jul. 25, 2000

Related U.S. Application Data (63) Continuation of application No. 09/160,970, filed on Sep. 25, 1998, now Pat. No. 6,240,393, which is a continuation-in-part of application No. 09/092,604, filed on Jun. 5, 1998, now Pat. No. 6,023,686, which is a continuation-in-part of application No. 08/603,131, filed on Feb. 20, 1996, now Pat. No. 5,794,219.

(51) Int. Cl.
*G06Q 99/00* (2006.01)
(52) U.S. Cl. .......................................................... 705/1
(58) Field of Classification Search ..................... 705/1
See application file for complete search history.

(56) References Cited

U.S. PATENT DOCUMENTS

| | | |
|---|---|---|
| 3,426,150 A | 2/1969 | Tygart |
| 3,566,365 A | 2/1971 | Rawson et al. |
| 3,566,370 A | 2/1971 | Worthington, Jr. et al. |
| 3,581,072 A | 5/1971 | Nymeyer |
| 3,768,014 A | 10/1973 | Smith |
| 3,811,116 A | 5/1974 | Takeuchi et al. |
| 3,883,235 A | 5/1975 | Lynn et al. |
| 3,910,257 A | 10/1975 | Fletcher et al. |

(Continued)

FOREIGN PATENT DOCUMENTS

EP   0286456   10/1988

(Continued)

OTHER PUBLICATIONS

Mavis, Brian E; Stoffelmayr, Bertram E, Multidimensional evaluation of monetary incentive strategies for weight control, The Psychological Record, Spring 1994.*

(Continued)

*Primary Examiner*—Jonathan Ouellette
(74) *Attorney, Agent, or Firm*—Suiter Swantz pc llo (57) ABSTRACT

The invention provides a method and system for aggregating and pooling information with feedback in a computer communication system. A communication system includes a server device and a set of client devices. Each client device collects information from an associated individual (whether by asking questions of those individuals, or accepting data input from peripheral devices), and transmits that data to a server device. The server device, or some other device at its behest, determines statistical information with regard to that data (such as aggregate, correlation, dispersion, or other measures), and provides that information to a communication channel for distribution to the individuals. The communication channel can include either (1) a broadcast communication channel that members of an affinity group can display, or (2) redistributing the determined statistical measures to associated individuals using the client devices. The statistical measure (such as an aggregate or sum) can be computed and distributed for the entire population, or can be computed and compared for selected sub-populations as a contest.

13 Claims, 2 Drawing Sheets

U.S. PATENT DOCUMENTS

| | | |
|---|---|---|
| 3,920,005 A | 11/1975 | Gombrich et al. |
| 3,996,928 A | 12/1976 | Marx |
| 4,004,577 A | 1/1977 | Sarnoff |
| 4,051,522 A | 9/1977 | Healy et al. |
| 4,060,915 A | 12/1977 | Conway |
| 4,130,881 A | 12/1978 | Haessler et al. |
| 4,150,284 A | 4/1979 | Trenkler et al. |
| 4,151,407 A | 4/1979 | McBride et al. |
| 4,151,831 A | 5/1979 | Lester |
| 4,173,971 A | 11/1979 | Karz |
| 4,216,462 A | 8/1980 | McGrath et al. |
| 4,227,526 A | 10/1980 | Goss |
| 4,253,521 A | 3/1981 | Savage |
| 4,259,548 A | 3/1981 | Fahey et al. |
| 4,270,547 A | 6/1981 | Steffen et al. |
| 4,296,756 A | 10/1981 | Dunning et al. |
| 4,347,568 A | 8/1982 | Giguere et al. |
| 4,347,851 A | 9/1982 | Jundanian |
| 4,360,345 A | 11/1982 | Hon |
| 4,412,287 A | 10/1983 | Braddock, III |
| 4,417,306 A | 11/1983 | Citron et al. |
| 4,422,081 A | 12/1983 | Woods |
| 4,428,733 A | 1/1984 | Kumar-Misir |
| 4,449,536 A | 5/1984 | Weaver |
| 4,465,077 A | 8/1984 | Schneider |
| 4,473,884 A | 9/1984 | Behl |
| 4,518,361 A | 5/1985 | Conway |
| 4,519,398 A | 5/1985 | Lisiecki et al. |
| 4,531,527 A | 7/1985 | Reinhold, Jr. et al. |
| 4,546,436 A | 10/1985 | Schneider et al. |
| 4,566,461 A | 1/1986 | Lubell et al. |
| 4,576,578 A | 3/1986 | Parker et al. |
| 4,592,546 A | 6/1986 | Fascenda et al. |
| 4,627,445 A | 12/1986 | Garcia et al. |
| 4,674,652 A | 6/1987 | Aten et al. |
| 4,685,059 A * | 8/1987 | Yamamoto ............... 422/82.05 |
| 4,686,624 A | 8/1987 | Blum et al. |
| 4,694,490 A | 9/1987 | Harvey et al. |
| 4,695,954 A | 9/1987 | Rose et al. |
| 4,712,562 A | 12/1987 | Ohayon et al. |
| 4,722,349 A | 2/1988 | Baumberg |
| 4,729,381 A | 3/1988 | Harada et al. |
| 4,730,253 A | 3/1988 | Gordon |
| 4,731,726 A | 3/1988 | Allen, III |
| 4,738,451 A | 4/1988 | Logg |
| 4,768,229 A | 8/1988 | Benjamin et al. |
| 4,779,199 A | 10/1988 | Yoneda et al. |
| 4,782,511 A | 11/1988 | Nemec et al. |
| 4,789,928 A | 12/1988 | Fujisaki |
| 4,796,639 A | 1/1989 | Snow et al. |
| 4,799,156 A | 1/1989 | Shavit et al. |
| 4,799,199 A | 1/1989 | Scales, III et al. |
| 4,803,625 A * | 2/1989 | Fu et al. ..................... 600/483 |
| 4,835,372 A | 5/1989 | Gombrich et al. |
| 4,838,275 A | 6/1989 | Lee |
| 4,846,797 A | 7/1989 | Howson et al. |
| 4,853,521 A | 8/1989 | Claeys et al. |
| 4,858,354 A | 8/1989 | Gettler |
| 4,858,617 A | 8/1989 | Sanders |
| 4,890,621 A | 1/1990 | Hakky |
| 4,894,777 A | 1/1990 | Negishi et al. |
| 4,897,869 A | 1/1990 | Takahashi |
| 4,899,839 A | 2/1990 | Dessertine et al. |
| 4,903,201 A | 2/1990 | Wagner |
| 4,907,973 A | 3/1990 | Hon |
| 4,931,934 A | 6/1990 | Snyder |
| 4,933,873 A | 6/1990 | Kaufman et al. |
| 4,933,876 A | 6/1990 | Markoff et al. |
| 4,950,246 A | 8/1990 | Muller |
| 4,950,264 A | 8/1990 | Osborn, III |
| 4,953,552 A | 9/1990 | DeMarzo |
| 4,958,632 A | 9/1990 | Duggan |
| 4,958,641 A | 9/1990 | Digby et al. |
| 4,967,756 A | 11/1990 | Hewitt |
| 4,977,899 A | 12/1990 | Digby et al. |
| 4,978,303 A | 12/1990 | Lampbell |
| 4,978,335 A | 12/1990 | Arthur, III |
| 4,979,509 A | 12/1990 | Hakky |
| 5,007,429 A | 4/1991 | Treatch et al. |
| 5,009,645 A | 4/1991 | Silver et al. |
| 5,016,172 A | 5/1991 | Dessertine |
| 5,019,974 A | 5/1991 | Beckers |
| 5,024,225 A | 6/1991 | Fang |
| 5,025,374 A | 6/1991 | Roizen et al. |
| 5,034,807 A | 7/1991 | Von Kohorn |
| 5,035,625 A | 7/1991 | Munson et al. |
| 5,036,462 A | 7/1991 | Kaufman et al. |
| 5,049,487 A | 9/1991 | Phillips et al. |
| 5,050,612 A | 9/1991 | Matsumura |
| 5,056,059 A | 10/1991 | Tivig et al. |
| 5,059,394 A | 10/1991 | Phillips et al. |
| 5,065,315 A | 11/1991 | Garcia |
| 5,068,536 A | 11/1991 | Rosenthal |
| 5,074,317 A | 12/1991 | Bondell et al. |
| 5,077,476 A | 12/1991 | Rosenthal |
| 5,077,665 A | 12/1991 | Silverman et al. |
| 5,095,798 A | 3/1992 | Okada et al. |
| 5,104,380 A | 4/1992 | Holman et al. |
| 5,109,414 A | 4/1992 | Harvey et al. |
| 5,109,974 A | 5/1992 | Beer et al. |
| 5,111,396 A | 5/1992 | Mills et al. |
| 5,111,817 A | 5/1992 | Clark et al. |
| 5,111,818 A | 5/1992 | Suzuki et al. |
| 5,120,230 A | 6/1992 | Clark et al. |
| 5,120,421 A | 6/1992 | Glass et al. |
| 5,128,752 A | 7/1992 | Von Kohorn |
| 5,134,391 A | 7/1992 | Okada |
| 5,142,358 A | 8/1992 | Jason |
| 5,142,484 A | 8/1992 | Kaufman et al. |
| 5,143,378 A | 9/1992 | Joel |
| 5,171,977 A | 12/1992 | Morrison |
| 5,176,502 A | 1/1993 | Sanderson et al. |
| 5,182,707 A | 1/1993 | Cooper et al. |
| 5,204,670 A | 4/1993 | Stinton |
| 5,219,322 A | 6/1993 | Weathers |
| 5,222,020 A | 6/1993 | Takeda |
| 5,226,895 A | 7/1993 | Harris |
| 5,227,874 A | 7/1993 | Von Kohorn |
| 5,228,450 A | 7/1993 | Sellers |
| 5,230,629 A | 7/1993 | Buschke |
| 5,231,990 A | 8/1993 | Gauglitz |
| 5,243,515 A | 9/1993 | Lee |
| 5,249,044 A | 9/1993 | Von Kohorn |
| 5,251,126 A | 10/1993 | Kahn et al. |
| 5,261,401 A | 11/1993 | Baker et al. |
| 5,262,943 A | 11/1993 | Thibado et al. |
| 5,265,888 A | 11/1993 | Yamamoto et al. |
| 5,266,179 A | 11/1993 | Nankai et al. |
| 5,275,159 A | 1/1994 | Griebel |
| 5,282,950 A | 2/1994 | Dietze et al. |
| 5,295,491 A | 3/1994 | Gevins |
| 5,299,121 A | 3/1994 | Brill et al. |
| 5,301,105 A | 4/1994 | Cummings, Jr. |
| 5,304,112 A | 4/1994 | Mrklas et al. |
| 5,304,468 A | 4/1994 | Phillips et al. |
| 5,307,263 A | 4/1994 | Brown |
| 5,309,919 A | 5/1994 | Snell et al. |
| 5,321,009 A | 6/1994 | Baeder et al. |
| 5,325,288 A | 6/1994 | Satou |
| 5,329,459 A | 7/1994 | Kaufman et al. |
| 5,329,608 A | 7/1994 | Bocchieri et al. |
| 5,331,549 A | 7/1994 | Crawford, Jr. |
| 5,333,981 A | 8/1994 | Pronovost et al. |
| 5,335,338 A | 8/1994 | Proesel |

| | | | | | |
|---|---|---|---|---|---|
| 5,339,821 A | 8/1994 | Fujimoto | 5,640,569 A | 6/1997 | Miller et al. |
| 5,341,291 A | 8/1994 | Roizen et al. | 5,640,953 A | 6/1997 | Bishop et al. |
| 5,343,239 A | 8/1994 | Lappington et al. | 5,642,731 A | 7/1997 | Kehr |
| 5,344,324 A | 9/1994 | O'Donnell et al. | 5,642,936 A | 7/1997 | Evans |
| 5,357,427 A | 10/1994 | Langen et al. | 5,651,363 A | 7/1997 | Kaufman et al. |
| 5,366,896 A | 11/1994 | Margrey et al. | 5,651,775 A | 7/1997 | Walker et al. |
| 5,368,562 A | 11/1994 | Blomquist et al. | 5,659,691 A | 8/1997 | Durward et al. |
| 5,371,687 A | 12/1994 | Holmes, II et al. | 5,666,487 A | 9/1997 | Goodman et al. |
| 5,375,604 A | 12/1994 | Kelly et al. | 5,670,711 A | 9/1997 | Detournay et al. |
| 5,377,100 A | 12/1994 | Pope et al. | 5,675,635 A | 10/1997 | Vos et al. |
| 5,390,238 A | 2/1995 | Kirk et al. | 5,678,562 A | 10/1997 | Sellers |
| 5,399,821 A | 3/1995 | Inagaki et al. | 5,678,571 A | 10/1997 | Brown |
| 5,410,471 A | 4/1995 | Alyfuku et al. | 5,679,075 A | 10/1997 | Forrest et al. |
| 5,410,474 A | 4/1995 | Fox | 5,680,590 A | 10/1997 | Parti |
| 5,429,140 A | 7/1995 | Burdea et al. | 5,680,866 A | 10/1997 | Kangas et al. |
| 5,431,690 A | 7/1995 | Schaldach et al. | 5,687,322 A | 11/1997 | Deaton et al. |
| 5,431,691 A | 7/1995 | Snell et al. | 5,687,717 A | 11/1997 | Halpern et al. |
| 5,434,611 A | 7/1995 | Tamura | 5,687,734 A | 11/1997 | Dempsey et al. |
| 5,438,607 A | 8/1995 | Przygoda, Jr. et al. | 5,689,652 A | 11/1997 | Lupien et al. |
| 5,438,983 A | 8/1995 | Falcone | 5,692,906 A | 12/1997 | Corder |
| 5,441,047 A | 8/1995 | David et al. | 5,704,364 A | 1/1998 | Saltzstein et al. |
| 5,449,334 A | 9/1995 | Kingsbury | 5,704,366 A | 1/1998 | Tacklind et al. |
| 5,454,721 A | 10/1995 | Kuch | 5,704,902 A | 1/1998 | Vandenbelt et al. |
| 5,454,722 A | 10/1995 | Holland et al. | 5,704,922 A | 1/1998 | Brown |
| 5,456,606 A | 10/1995 | McIntyre | 5,710,178 A | 1/1998 | Samid |
| 5,456,692 A | 10/1995 | Smith, Jr. et al. | 5,710,918 A | 1/1998 | Lagarde et al. |
| 5,458,123 A | 10/1995 | Unger | 5,711,297 A | 1/1998 | Iliff |
| 5,467,269 A | 11/1995 | Flaten | 5,714,319 A | 2/1998 | Joutel et al. |
| 5,471,039 A | 11/1995 | Irwin, Jr. et al. | 5,715,451 A | 2/1998 | Marlin |
| 5,471,382 A | 11/1995 | Tallman et al. | 5,715,823 A | 2/1998 | Wood et al. |
| 5,483,276 A | 1/1996 | Brooks et al. | 5,717,739 A | 2/1998 | Dyer et al. |
| 5,488,412 A | 1/1996 | Majeti et al. | 5,717,913 A | 2/1998 | Driscoll |
| 5,488,423 A | 1/1996 | Walkingshaw et al. | 5,720,733 A | 2/1998 | Brown |
| 5,501,231 A | 3/1996 | Kaish | 5,722,418 A | 3/1998 | Bro |
| 5,502,636 A | 3/1996 | Clarke | 5,727,153 A | 3/1998 | Powell |
| 5,502,726 A | 3/1996 | Fischer | 5,730,124 A | 3/1998 | Yamauchi |
| 5,504,519 A | 4/1996 | Remillard | 5,730,654 A | 3/1998 | Brown |
| 5,517,405 A | 5/1996 | McAndrew et al. | 5,732,696 A | 3/1998 | Rapoport et al. |
| 5,518,001 A | 5/1996 | Snell | 5,732,709 A | 3/1998 | Tacklind et al. |
| 5,519,058 A | 5/1996 | Gonick et al. | 5,734,413 A | 3/1998 | Lappington et al. |
| 5,519,433 A | 5/1996 | Lappington et al. | 5,749,083 A | 5/1998 | Koda et al. |
| 5,523,232 A | 6/1996 | Sechler | 5,752,234 A | 5/1998 | Withers |
| 5,536,249 A | 7/1996 | Castellano et al. | 5,754,740 A | 5/1998 | Fukuoka et al. |
| 5,542,420 A | 8/1996 | Goldman et al. | 5,760,771 A | 6/1998 | Blonder et al. |
| 5,544,649 A | 8/1996 | David et al. | 5,772,585 A | 6/1998 | Lavin et al. |
| 5,546,943 A | 8/1996 | Gould | 5,778,882 A | 7/1998 | Raymond et al. |
| 5,549,117 A | 8/1996 | Tacklind et al. | 5,782,814 A | 7/1998 | Brown et al. |
| 5,550,575 A | 8/1996 | West et al. | 5,785,650 A | 7/1998 | Akasaka et al. |
| 5,553,609 A | 9/1996 | Chen et al. | 5,787,295 A | 7/1998 | Nakao |
| 5,558,638 A | 9/1996 | Evers et al. | 5,791,342 A | 8/1998 | Woodard |
| 5,564,429 A | 10/1996 | Bornn et al. | 5,792,117 A | 8/1998 | Brown |
| 5,569,212 A | 10/1996 | Brown | 5,793,969 A | 8/1998 | Kamentsky et al. |
| 5,572,421 A | 11/1996 | Altman et al. | 5,794,219 A | 8/1998 | Brown |
| 5,572,646 A | 11/1996 | Kawai et al. | 5,794,251 A | 8/1998 | Watanabe et al. |
| 5,574,828 A | 11/1996 | Hayward et al. | 5,796,393 A | 8/1998 | MacNaughton et al. |
| 5,576,952 A | 11/1996 | Stutman et al. | 5,799,318 A | 8/1998 | Cardinal et al. |
| 5,583,758 A | 12/1996 | McIlroy et al. | 5,800,458 A | 9/1998 | Wingrove |
| 5,590,648 A | 1/1997 | Mitchell et al. | 5,802,494 A | 9/1998 | Kuno |
| 5,593,349 A | 1/1997 | Miguel et al. | 5,802,534 A | 9/1998 | Hatayama et al. |
| 5,593,390 A | 1/1997 | Castellano et al. | 5,806,057 A | 9/1998 | Gormley et al. |
| 5,594,637 A | 1/1997 | Eisenberg et al. | 5,807,336 A * | 9/1998 | Russo et al. ............ 604/131 |
| 5,596,994 A | 1/1997 | Bro | 5,810,747 A | 9/1998 | Brudny et al. |
| 5,597,307 A | 1/1997 | Redford et al. | 5,819,735 A | 10/1998 | Mansfield et al. |
| 5,601,435 A | 2/1997 | Quy | 5,822,544 A | 10/1998 | Chaco et al. |
| 5,613,495 A | 3/1997 | Mills et al. | 5,822,715 A | 10/1998 | Worthington et al. |
| 5,619,991 A | 4/1997 | Sloane | 5,825,283 A | 10/1998 | Camhi |
| 5,624,265 A | 4/1997 | Redford et al. | 5,827,180 A | 10/1998 | Goodman |
| 5,628,309 A | 5/1997 | Brown | 5,828,943 A | 10/1998 | Brown |
| 5,629,981 A | 5/1997 | Nerlikar | 5,832,448 A | 11/1998 | Brown |
| 5,631,844 A | 5/1997 | Margrey et al. | 5,835,896 A | 11/1998 | Fisher et al. |
| 5,633,910 A | 5/1997 | Cohen | 5,840,020 A | 11/1998 | Heinonen et al. |
| 5,635,532 A | 6/1997 | Samid | 5,842,976 A | 12/1998 | Williamson |
| 5,639,471 A * | 6/1997 | Chait et al. ............ 424/439 | 5,868,669 A | 2/1999 | Iliff |

| | | | | | |
|---|---|---|---|---|---|
| 5,868,683 A | 2/1999 | Protopapas et al. | 6,248,065 B1 | 6/2001 | Brown |
| 5,875,432 A | 2/1999 | Sehr | 6,260,022 B1 | 7/2001 | Brown |
| 5,879,163 A | 3/1999 | Brown et al. | 6,269,343 B1 * | 7/2001 | Pallakoff ............. 705/26 |
| 5,882,338 A | 3/1999 | Gray | 6,270,455 B1 | 8/2001 | Brown |
| 5,887,133 A | 3/1999 | Brown et al. | 6,270,456 B1 | 8/2001 | Iliff |
| 5,893,077 A | 4/1999 | Griffin | 6,334,778 B1 | 1/2002 | Brown |
| 5,893,098 A | 4/1999 | Peters et al. | 6,352,523 B1 | 3/2002 | Brown et al. |
| 5,897,493 A * | 4/1999 | Brown ................ 600/300 | 6,368,273 B1 | 4/2002 | Brown |
| 5,899,855 A | 5/1999 | Brown | 6,370,513 B1 | 4/2002 | Kolawa et al. |
| 5,907,291 A * | 5/1999 | Chen et al. ......... 340/870.16 | 6,375,469 B1 | 4/2002 | Brown |
| 5,911,687 A | 6/1999 | Sato et al. | 6,379,301 B1 | 4/2002 | Worthington et al. |
| 5,913,310 A | 6/1999 | Brown | 6,381,577 B1 | 4/2002 | Brown |
| 5,913,826 A * | 6/1999 | Blank ................ 600/500 | 6,418,415 B1 * | 7/2002 | Walker et al. ......... 705/26 |
| 5,918,603 A | 7/1999 | Brown | 6,436,036 B1 | 8/2002 | Miller-Kovach et al. |
| 5,920,477 A | 7/1999 | Hoffberg et al. | 6,466,919 B1 * | 10/2002 | Walker et al. ......... 705/37 |
| 5,932,226 A * | 8/1999 | Ordman ................ 424/400 | 6,513,532 B2 * | 2/2003 | Mault et al. ......... 600/595 |
| 5,933,136 A | 8/1999 | Brown | 2002/0019748 A1 | 2/2002 | Brown |
| 5,935,060 A | 8/1999 | Iliff | 2002/0099691 A1 * | 7/2002 | Lore et al. ............ 707/2 |
| 5,940,801 A | 8/1999 | Brown | 2004/0106855 A1 | 6/2004 | Brown |
| 5,940,802 A * | 8/1999 | Hildebrand et al. ...... 705/3 | 2004/0107116 A1 | 6/2004 | Brown |
| 5,941,829 A | 8/1999 | Saltzstein et al. | 2004/0117207 A1 | 6/2004 | Brown |
| 5,945,651 A | 8/1999 | Chorosinski et al. | 2004/0117208 A1 | 6/2004 | Brown |
| 5,951,300 A | 9/1999 | Brown | 2004/0117209 A1 | 6/2004 | Brown |
| 5,954,641 A | 9/1999 | Kehr et al. | 2004/0117210 A1 | 6/2004 | Brown |
| 5,956,501 A | 9/1999 | Brown | | | |
| 5,960,403 A | 9/1999 | Brown | | | |
| 5,961,446 A | 10/1999 | Beller et al. | | | |

FOREIGN PATENT DOCUMENTS

| | | |
|---|---|---|
| EP | 0320749 | 6/1989 |
| EP | 370599 | 5/1990 |
| EP | 0461910 | 12/1991 |
| EP | 508912 | 10/1992 |
| EP | 526166 | 2/1993 |
| EP | 0558975 | 9/1993 |
| EP | 0653718 | 5/1995 |
| EP | 676709 | 10/1995 |
| EP | 680727 | 11/1995 |
| EP | 761160 | 3/1997 |
| EP | 08131551 | 12/1997 |
| EP | 0251520 | 1/1998 |
| GB | 2218831 | 11/1989 |
| GB | 2225637 | 6/1990 |
| JP | 54005785 | 1/1979 |
| JP | 54146633 | 11/1979 |
| JP | 62226278 | 10/1987 |
| JP | 5155024 | 6/1993 |
| JP | 5266002 | 10/1993 |
| JP | 1995407095963 | 4/1995 |
| WO | WO-8501667 | 4/1985 |
| WO | WO-90/00367 | 1/1990 |
| WO | WO-9109374 | 6/1991 |
| WO | WO-93/01489 | 1/1993 |
| WO | WO-9302622 | 2/1993 |
| WO | WO-9416774 | 8/1994 |
| WO | WO-95/09386 | 4/1995 |
| WO | WO-95/20199 | 7/1995 |
| WO | WO-9522131 | 8/1995 |
| WO | WO-9529447 | 11/1995 |
| WO | WO-96/07908 | 3/1996 |
| WO | WO-96/25877 | 8/1996 |
| WO | WO-9636923 | 11/1996 |
| WO | WO-97/08605 | 3/1997 |
| WO | WO-97/12544 | 4/1997 |
| WO | WO-9737738 | 10/1997 |
| WO | WO-98/16895 | 4/1998 |
| WO | WO-9839933 | 9/1998 |

| | | |
|---|---|---|
| 5,966,526 A | 10/1999 | Yokoi |
| 5,971,855 A | 10/1999 | Ng |
| 5,971,922 A | 10/1999 | Arita et al. |
| 5,983,003 A | 11/1999 | Lection et al. |
| 5,983,217 A | 11/1999 | Khosravi-Sichani et al. |
| 5,987,471 A | 11/1999 | Bodine et al. |
| 5,995,969 A | 11/1999 | Lee et al. |
| 5,997,476 A | 12/1999 | Brown |
| 5,997,502 A | 12/1999 | Reilly et al. |
| 6,001,065 A | 12/1999 | DeVito |
| 6,022,315 A | 2/2000 | Iliff |
| 6,022,615 A | 2/2000 | Rettenbacher |
| 6,023,686 A | 2/2000 | Brown |
| 6,024,281 A | 2/2000 | Shepley |
| 6,029,138 A | 2/2000 | Khorasani et al. |
| 6,032,119 A | 2/2000 | Brown et al. |
| 6,035,328 A | 3/2000 | Soukal |
| 6,046,761 A | 4/2000 | Echerer |
| 6,049,794 A | 4/2000 | Jacobs et al. |
| 6,050,940 A | 4/2000 | Braun et al. |
| 6,055,314 A | 4/2000 | Spies et al. |
| 6,055,487 A | 4/2000 | Margery et al. |
| 6,055,506 A | 4/2000 | Frasca, Jr. |
| 6,057,758 A | 5/2000 | Dempsey et al. |
| 6,068,615 A | 5/2000 | Brown et al. |
| 6,101,478 A | 8/2000 | Brown |
| 6,110,148 A | 8/2000 | Brown et al. |
| 6,113,578 A | 9/2000 | Brown |
| 6,128,599 A * | 10/2000 | Walker et al. ......... 705/14 |
| 6,138,145 A | 10/2000 | Kawanaka |
| 6,144,837 A | 11/2000 | Quy |
| 6,151,586 A | 11/2000 | Brown |
| 6,161,095 A | 12/2000 | Brown |
| 6,167,362 A | 12/2000 | Brown et al. |
| 6,167,386 A * | 12/2000 | Brown ................ 705/37 |
| 6,168,563 B1 | 1/2001 | Brown |
| 6,177,940 B1 | 1/2001 | Bond et al. |
| 6,186,145 B1 | 2/2001 | Brown |
| 6,189,029 B1 | 2/2001 | Fuerst |
| D439,242 S | 3/2001 | Brown et al. |
| 6,210,272 B1 | 4/2001 | Brown |
| 6,221,012 B1 | 4/2001 | Maschke et al. |
| 6,233,539 B1 | 5/2001 | Brown |
| 6,240,393 B1 | 5/2001 | Brown |
| 6,246,975 B1 * | 6/2001 | Rivonelli et al. ......... 703/11 |
| 6,246,992 B1 * | 6/2001 | Brown ................ 705/2 |

OTHER PUBLICATIONS

Yoshizawa, Daisuke, et al., "The Development of a Data Processing System with Personal Computer MSX Standard System for Flow Injection Analysis", Journal of Flow Injection Analysis, (1988), V.5, No. 2, pp. 101-110.

Jaffrey et al.; "PIN: An Assocaited Protein Inhibitor of Neuronal Nitric Oxide Synthase"; Science; vol. 274; Nov. 1, 1996; Ref: XP 002050141.

"Blood Glucose Monitors", Portable Health Device, (1998), vol. 17(9), pp. 253-271.

"Talking Nano Puppy"; retrieved from URL http://www.virtualpet.com/vp/farm/nano/talkn/talkn.htm Apr. 23, 2000.

Voelker, Rebecca, "Shoe Leather Therapy is Gaining on TB", Jama, (Mar. 13, 1996), vol. 275, 743.

"Digital Doggie"; retrieved from URL http://www.virtualpet.com/vp/farm/gigapet/ddoggie.htm Apr. 23, 2000.

ANONYMOUS, "Health Hero Network, Inc. Receives First-Ever FDA Clearance for Connecting Medical Devices to Internet", PR Newswire, (Dec. 2, 1993), 3 pages.

"Playmates Toys deals knockout blow to virtual pet competitors with introduction of Nano Fighter™ For Boys"; New Nano Pet Fighting Pet Press Release; retrieved from URL http://www.virtualpet.com/vp/farm/nano/nfightpr.htm Apr. 23, 2000.

UPDIKE, Stuart J., et al., "Laboratory Evaluation of New Reusable Blood Glucose Sensor", Diabetes Care, (Nov./Dec. 1998), vol. 11, No. 10, pp. 801-807.

RO_AUCTION Auctioneers Property Database System and RO_Auction Auctioneers Accounting System; RO-AUCTION features; Dec. 04 1995.

Fabietti, P.G., et al., "Wearable System for Acquisition, Processing and Storage of the Signal from Amperometric Glucose Sensors", The International Journal of Artificial Organs, (1991), vol. 14, No. 3, pp. 175-178.

Reis, H, "Telemedicine: Transmitting Expertise to the Point of Care Toward an Electronic Patient Record"; '97, Nashville, TN, Apr. 27-May 3, 1997, pp. 248-256, v. 3.

Shults, Marc C., et al., "A Telemetry-Instrumentation System for Monitoring Multiple Subcutaneously Implanted Glucose Sensors", IEEE Transactions on Biomedical Engineering, (Oct. 1994), vol. 41, No. 10, pp. 937-942.

United Healthcare's OPTUM Division goes online to better health by announcing a unique internet application. PR Newswire, p0801MNTH004. Aug. 1, 1996.

Hunter, "Technological Advances in Bedside Monitoring: Biosensors", Archives and Laboratory Medicine, (Jul. 1987), pp. 633-636.

Telemedicine Provides Two-Way Computer Link For Parents of Very Premature Infants. PR Newswire, p1007NEM034. Oct. 7, 1996.

Schrezenmeir, J. et al., "Computer Assisted Dosage Adjustment—Perspective for Diabetes Control", Hormone and Metabolic Research, Supplement Series, (1990), vol. 24, pp. 116-123.

Save the earth artrock auction, http://www.commerce.com.saceearth. Auction Web, http://www.ebay.com.

Makikawa, M., et al., "Microprocessor-Based Memory Device for Ambulatory Heart Rate and and Physical Activity Recording", Methods of Information in Medicine, (1994), vol. 33, No. 1, pp. 94-96.

Luebke, Cathy, "Barrett-Jackson Auction Turns High-Tech", Business Journal, vol. 16, Issue 12, pp. 11, Jan. 19, 1996.

Schenkels, P., "Supplementary European Search Report", Application No. EP 97 92 2716, (Mar. 11, 2002).

"Theme Hospital," product review 1996 [retrieved Apr. 21, 2000], Retrieved from <URL:www.vigilante.co.uk/ep/misc/hospital.htm>.

Potter, David, "Fundamentals of PC-Based Data Acquisition", SENSORS, (Feb. 1994), pp. 12-20.

"Virtual Tomagutchi," 1998 [retrieved Apr. 23, 2000], Retrieved from <URL:www.sttf.org/english/action/tomagutchi.html>.

Roberts; "Diabetes and Stress: A Type A Connection?", Psychology Today, (Jul. 1987), v. 21; pp. 22(1); Dialog: File 149, Acc#05038381.

"Virtual Pet Product Reviews," 1997 [retrieved on Apr. 23, 2000], Retrieved from <URL:www.virtualpet.com/vp/farm/reviews/reviews,htm>.

Soeldner, J. S., "Treatment of Diabetes Mellitus by Devices", The American Journal of Medicine, (Jan. 1981), vol. 70, 183-194.

"Giga Pets," 1997 [retrieved on Apr. 23, 2000], Retrieved from <URL:www.virtualpet.com/vp/farm/gigapet/gigapet.htm>.

Poitout, V., et al. "A Glucose Monitoring System for On Line Estimation in Man of Blood Glucose Concentration Using a Miniaturized Glucose Sensor Implanted in the Subcutaneous Tissue and a Wearable Control Unit", Diabetologia, (1993), vol. 36, pp. 658-663.

Polson, Gary "Recent Developments and Trends in Keychain Virtual Pets," 1997 [retrieved on Apr. 23, 2000], Retrieved from <URL:www.virtualpet.com/vp/future/trends1a.htm>.

Franklin; "Proposed Auction Rules for PCS: The FCC Plans to Use Competitive Bidding, but Exact Procedures are Undefined"; Cellular Business; v10 n13; p. 18(2); Dec. 1993; DIALOG: File 148, Acc#06787310.

"Towards a partnership of care", M2 Presswire, Jun. 14, 2000.

Moore, "New Applications Break Through Storage Boundaries", Computer Technology Review, (Oct. 1999), vol. 19, No. 10 p. 1.

"Who Will Dominate The Desktop in the 90's?", Jack Shandle, Electronics, Feb. 1990, pp. 48-50. (3 pages) Cited by 2 patents.

Howey, et al., "A Rapidly Absorbed Analogue of Human Insulin"; Diabetes, vol. 43, Mar. 1994, pp. 396-402. (7 pages).

Jimison et al., "Patient-Specific explanation in models of chronic disease", Revised Feb. 1992 Artificial Intelligence in Medicine 4 (1992) 191-205.

Mazzola, et al., "Video Diabetes: A Teaching Tool for Children with Insulin-Dependent Diabetes", Proceedings—7th Annual Symposium on Computer Applications in Medical Care; Washington, DC; Dialog:, (Oct. 1983), File 8, Acc# 0624462.

Jones, Chris, "Microsoft readies DocObject; technology will allow document editing in Web browsers", infoWorld, v18 n18 p. 48(1), Apr. 29, 1996.

"AdOptimizer—Ad Management Software For Websites", Newsbytes, pNEW10040041, Oct. 4, 1996.

"New Horizons teams with Duke, Real Media"; The Seybold Report on Desktop Publishing, v10 n12 p. 24(1), Aug. 12, 1996.

Marsh, David G. "Approaches Toward the Genetic Analysis of Complex Traits Asthma and Atrophy", Am. J. Respir.Crit.Care Med., (1997), vol. 156, pp. S-133-S138.

Mims; "Psychological Testing"; Computers & Electronics; v23; p. 22(6); Feb. 1985; Dialog: File 47, Acc# 2654858.

Wilkins, Aaron. "Expanding Internet access for health care consumers", Health Care Management Review, Summer, Jul. 1999, 24-30.

Kennedy et al.; "Television Computer Games: A New Look in Performance Testing"; Aviat Space Environ Med; Jan. 1982, 53(1); pp. 49-53. (5 pages); Dialog Abstract: File 155, Acc#0353751.

Leyerle, Beverly J., et al., "The PDMS as a Focal Point for Distributed Patient Data", International Journal of Clinical Monitoring and Computing, (1988), vol. 5, pp. 155-161.

Furnham, et al; "Measuring Locus of Control: a Critique of General Children's Health- and Work-related Locus of Control Questionnaires"; British Journal of Psychology; v84 n4; p. 443(37); Nov. 1993; Dialog: File 88, Acc# 14903135.

Octogotchi Instruction Manual, 1997. Dino-Kun Instruction Manual, 1997.

Gardner, et al.; "Comprehension and Appreciation of Humorous Material Following Brain Damage"; Brain; Sep. 1975; 98(3); pp. 399-412; Dialog: File 153, Acc#02859983. (14 pages).

Latman, N.S., "Evaluation of Electronic, Digital Blood Glucose Monitors", Biomedical Instrumentation and Technology, (1991), vol. 25, No. 1, 43-49.

Edelson; "Fashion Reevaluates Flickering Fortunes of TV Home Shopping"; WWD; v170 n87; p. 1(3); Nov. 8, 1995; DIALOG: File 148, Acc#08289119.

Results of the world's first on-line auction, http://www.christies.com.

"Cathay Pacific Airways-USA to Hold First-Ever Internet CyberAuction; Cyber Travelers Can Bid for 50 Business Class Round Trips to Hong-Kong—No Minimum Bid"; Business Wire; p9261084; Sep. 26, 1995; DIALOG: File 148, Acc#08167091.

Kuykendall, V.G., et al., "Assessment of Self-Monitored Blood Glucose results Using a Reflectance Meter with Memory and Microcomputer", Symposium on Computer Applications in Medical Care, (Jan. 1981), vol. 70, pp. 98-102.

"ONSALE Onsale Brings Thrill of Auctions and Bargain Hunting Online; Unique Internet retail service debuts with week-long charity auction for the Computer Museum in Boston", May 24, 1995; Dialog Abstract: File 610, Acc#0489267.

"Playmates Toys leads Americas virtual pet craze into its next generation by introducing talking Nano Pals"; Talking Nano Pet Press Release; Nov. 18, 1997; retrieved from URL http://www.virtualpet.com/vp/farm/nano/talkn/tnpress.htm on Apr. 23, 2000.

O'Donnell; "Alan's At It Again"; Bond Buyer; v309 n29448; p. 1(3); Jul. 21, 1994; DIALOG: File 148, Acc#07478152.

Kauffmann, et al., "Epidemiological Study of the Genetics and Environment of Asthma, Bronchial Hyperresponsiveness and Atrophy", Am. J. Respir. Crit. Care Med., (1997), vol. 156, pp. S123-S129.

Gautlet (for PC) rulebook by Mindscape Inc. (Gauntlet by Apple);1985.

Brenman et al.; "Interaction of Nitric Oxide Synthase with the Postsynaptic Density Protein PSD-95 and α1-Syntrophin Mediated by PDZ Domains"; Cell; vol. 84, pp. 757-767, Mar. 8, 1996; Ref: XP-002104701.

Bai, "Design of home healthcare network", IEEE 1997 pp. 1657-1658.

Horio, Hiroyuki, et al., "Clinical Telecommunication Network System for Home Monitoring", Medical & Biological Engineering & Computing, (Mar. 1994), vol. 32, 227-230.

"The description of the Tandy Radio Shack TRS-80 Model 100/102 device available at http://www.old-computuers.com/musuem/computer.asp?c=233", World Wide Web, (Feb. 13, 2004), 1-3.

Brunetti, P., et al., "A Simulation Study on a Self-Turning Portable Controller of Blood Glucose", The International Journal of Artificial Organs, (1993), vol. 16, No. 16, pp. 51-57.

Cheng, Joe H., "PCT Search Report", (Jan. 11, 1996).

Hauben, Jay R., "A Brief History of the Cleveland Free-Net", available at http://www.ais.org/~irh/acn7-1.a09.html, (1995) pp. 1-4.

Hauser, et al., "Will Computers Replace or Complement the Diabetes Educator?", The Medical Journal of Austrailia, (Oct. 5, 1992), vol. 157, 489-491.

Lacyk, John, "PCT Search Report", (Jun. 12, 1997).

Miles, Laughton E., "A Portable Microcomputer for Long-Term Physiological Monitoring in the Home and Work Environment", Medical Monitoring in the Home and Work Environment, (1990) pp. 47-57.

Giuffrida, et al., Should We Pay the Patient? Review of Financial Incentives to enhance Patient Compliance:, Biomedical Journal, (1997), vol. 315, pp. 703-707.

Pfeiffer, E. F., "The Glucose Sensor: The Missing Link in Diabetes Therapy", Hormone and Metabolic Research, (1990), vol. 24m Suppl. pp. 154-164.

Schork, Nicholas J, "Genetics of Complex Disease", Am.J.Respir. Crit. Care Me., (1997), vol. 156, pp. S103-S109.

Shandle Jack, "Who will dominate the desktop In the 90's?", Electronics, (Feb. 1990), pp. 46-50.

Finston, "Parent+Teacher=Healthy Child", Diabetes Forecast, (Apr. 1994), v47 n9; p. 26(5); Dialog: file 149, Acc# 15804228.

M.U.L.E. rulebook by Electronic Arts, 1983.

"Onsale Joins Fray as Online Shopping Picks Up Speed: Internet Booms"; Computer Reseller News; Jun. 5, 1995; p. 73; DIALOG: File 16, Acc#05649796.

Siegmann;"Nowhere to Go but Up"; PC Week; v12 n42, p. A5(1); Oct. 23, 1995; DIALOG: File 148, Acc#08222496.

Douglas, A.S., et al., "Hand-Held Glucose Monitor and Recorder", Proceedings of the Annual International Conference of the IEEE Engineering in Medicine and Biology Society, New Orleans, LA, (Nov. 1988), pp. 747-748.

Adilman; "Videogames: Knowing the Score"; Creative Computing; v9; p. 224(5); Dec. 1983; Dialog: File 148, Acc# 01891055.

Marx, Wendy, "More than just the Scores: ESPNET SportsZone is a model for expanding brand names online", InformationWeek, n576 p. 61(2), Apr. 22, 1996.

Skolnick et al. "Simultaneous Analysis of Multiple Polymorphic Loci Using Amplified Sequence Polymorphisms (ASPs)"; Genomics. 2: 273-279.

Caprihan, A., et al., "A Simple Microcomputer for Biomedical Signal Processing", IECI '78 Annual Conference Proceedings on Industrial Applicatoins of Microprocessors, (Mar. 20, 1978), 18-23.

"Tamagotchi," 1997 [retrieved on Apr. 23, 2000], Retrieved from <URL:www.virtualpet.com/vp/farm/lleg/lleg.htm>.

"Putting the Lot on the Net", Antique Collector, vol. 66, Issue 9, p. 26, Downloaded from Corporate Resource Net, Nov./Dec. 1995.

Lachnit, Carroll, "Hawkin's Online Auction", Photo District News, vol. 16, Issue 1, p. 18, Jan. 1996.

Bruce, "Health Hero Network CEO, CNNfn", Digital Jam, (Dec. 1, 1999), 3.

"Cathay Pacific Airways-USA receives more than 1,300 bids during first five days of CyberAuction"; Business Wire, Oct. 18, 1995, p. 10181119.

"Nano Fighter Pets", retrieved from URL http://www.virtualpet.com/vp/farm/nano/nfighter.htm Apr. 23, 2000.

"Giga Farm"; retrieved from URL http://www.virtualpet.com/vp/farm/gigapet/gpfarm/gpfarm.htm Apr. 23, 2000.

Billiard, A., et al. "Telematic Transmission of Computerized Blood Glucose Profiles for IDDm Patients", Diabetes Care, (Feb. 1991), vol. 14, No. 2, pp. 130-134.

Bower, "Brain Clues to Energy-efficient Learning", Science News, (Apr. 1992), v. 141; p. 215(1); Dialog: File 647, Acct#12123949.

Frieberger, Paul, "Video Game Takes on Diabetes Superhero 'Captain Novolin' Offers Treatment Tips", San Francisco Examiner, (Jun. 26, 1992), Fourth Edition, Business Section B1.

Kaufman, Steven, B., "The Learning Game"; Nation's Business, (Nov. 1993).

Albisser, A.M. "Intelligent Instrumentation in Diabetic Management", CRC Critical Reviews in Biomedical Engineering, vol. 17, No. 1, pp. 1-24.

Rose, V. L., et al., "Decentralized Testing for Prothrombin Time and Activated Partial Thromboplastin Time Using a Dry Chemistry Portable Analyser", Archives of Pathology and Laboratory Medicine, (Jun. 1993), vol. 117, pp. 611-617.

Wyatt, J. C., "Clinical Data Systems, Part 2: Components and Techniques", Lancet, (Dec. 1994), vol. 344, No. 8937, pp. 1609-1614.

Gordon; "Auctions Become High Tech"; Dealer Business; v29 n7; p. 21(4); Mar. 1995; DIALOG: File 148, Acc™07862519.

"Introducing the Next Generation of About Your Diabetes"; U.S. Pharmacopical Convention and American Diabetes Association, (1993).

Hutheesing, Nikhil "An on-line gamble", Forbes, v157 n10 p. 288(1), May 20, 1996.

"Future of the Virtual Pet Industry," 1997 [retrieved on Apr. 23, 2000], Retrieved from <URL:www.virtualpet.com/vp/ future/future.htm>.

DigiPet Instruction Manual, 1997.

"European Search Report", From 6858P005EP, (Mar. 27, 1998).

"Nano Baby Instructions"; retrieved from file://C:\My Documents\Nano Baby Instructions.htm Apr. 23, 2000.

"How Flash Memory Works", Internet printout of URL address: http://www.howstuffworks.com/flash-memory4.htm, (Sep. 28, 2002), 2 pages.

FOX, "Not My Type: Type B Behavior, Type I Diabetes Plus Stress Equals Blood Sugar Blues", Health, (Mar. 1998), v20 n3; pp. 22(1); Dialog: File 149, Acc# 06397959.

"CD-ROM Mavericks: Proprietary TV-Based Players", Byte Guide to CD-ROM, pp. 100-105.

Vallera, D. A., et al., "Accuracy of Portable Blood Glucose Monitoring", American Journal of Clinical Pathology, (1991), vol. 95, No. 2, pp. 247-252.

Valla, et al., "A Structured Pictorial Questionnaire to Assess DSM-III-R-based Diagnosis in Children (6-11 years)"; Journal of Abnormal Child Psychology; v22 n4; p. 403(21); Aug. 1994; Dialog: File 88, Acc# 15759542.

Nano Page, 1997 [retrieved on Apr. 23, 2000], Retrieved from <URL:www.virtualpet.com/vp/farm/nano/nano.htm>.

"+5V Powered Isolated RS-232 Drivers/Receivers" Maxim Integrated Products.

"Central Fetal Monitoring Systems with Optical Disk Storage", New Technology Brief, (Nov./Dec. 1998), vol. 2, No. 6, pp. 249-251.

Meissner, et al., "Building an Integrated Clinical and Research Network", Proceedings of the SPIE, (Oct. 24, 1995), vol. 2618, p. 92-99.

Bruce, et al., "The Effects of Sympathetic Nervous System Activation and Psychological Stress . . . "; Diabetologia; 35(9); 1992; 835-843; Dialog: File 5, Acc#9629427. (9 pages).

Schement, "An Intelligent Controller for Neurophysiological Experiments," Proceeding of the Annual Symposium on Computer Based Medical Systems, Durham, Jun. 14-17, 1992, p. 528, line 1—p. 529, line 21.

Martinez, Fernando D., "Complexities of the Genetics of Asthma", Am.J. Respir. Crit. Care Med., (1997), vol. 156, pp. S117-S122.

Spitzer et al.; "The moderating effect of age on self-care"; Western Journal Of Nursing Research, v18, n2, p. 136(13), Apr. 1996.

Reserach project launched to improve health of America's communities; new Disney community in Florida is focus of program. Business Wire, p. 10011142. Oct. 1, 1996.

McCullagh, PJ et al., "Computerized paradigms for eliciting the contingent negative variation event-related potential," Proceedings of the Annual International Conference of the Engineering in Medicine & Biology Society, IEEE, Conf. 14, p. 2481-2483, Oct. 1992.

* cited by examiner

AGGREGATING AND POOLING HEALTH RELATED INFORMATION IN A COMMUNICATION SYSTEM WITH FEEDBACK

The present application is a continuation of U.S. patent application Ser. No. 09/160,970 filed Sep. 25, 1998, now U.S. Pat. No. 6,240,393, which is a continuation in part of U.S. patent application Ser. No. 09/092,604 filed Jun. 5, 1998, now U.S. Pat. No. 6,023,686, which is a continuation in part of U.S. patent application Ser. No. 08/603,131 filed Feb. 20, 1996, now U.S. Pat. No. 5,794,219.

BACKGROUND OF THE INVENTION

1. Field of the Invention

This invention relates to aggregating and pooling information.

2. Related Art

In programs that have a number of participants, it sometimes is desirable to aggregate information from those participants, so as to indicate to individuals in a population when the population (or a subset of that population) is achieving a selected goal. For example, in fund-raising events for an affinity group, it is often desirable to publicize to the individuals the progress of the fund-raising event toward a selected goal. Similarly, in an affinity group such as a weight-loss club, it would be advantageous to be able to publicize the collective results of the efforts of individuals in the affinity group.

One problem in the known art is that of collecting information from diverse sources, aggregating that information, and presenting that information to the individual members of the population. This problem is particularly exacerbated if the information to be collected is not available in any single location, and is further exacerbated if the individuals to receive the information to be publicized are not available in any single location.

The known art includes methods for aggregating and pooling information for bidding or otherwise conducting auctions using distributed communication systems. Some of these known methods include systems described as known art in the following applications:

U.S. Pat. No. 6,023,686, "Method for Conducting an On-Line Bidding Session with Bid Pooling," filed Jun. 5, 1998, in the name of the same inventor, and assigned to the same assignee;

U.S. application Ser. No. 08/603,131, filed Feb. 20, 1996, issued on Aug. 11, 1998, as U.S. Pat. No. 5,794,219, in the name of the same inventor, and assigned to the same assignee.

These applications are hereby incorporated by reference as if fully set forth herein, and are collectively referred to herein as the "On-Line Bidding Disclosures." Although these applications describe other known art, no admission is made herein that any part of these applications are themselves known in the art.

In the On-Line Bidding Disclosures, individual users, coupled to a system using a communication network, are able to enter values into their client devices. The individual values are collected at a server device or other data clearinghouse. The individual values are aggregated or pooled. The aggregated or pooled information is used to determine whether the individual users, either individually or in sub-populations, are winners of the on-line auction.

Accordingly, it would also be advantageous to aggregate or pool information (whether medical, financial, or otherwise) so that the collective information could be publicized to participating individuals. This would be particularly advantageous in encouraging members of an affinity group to promote their individual efforts so as to cause the collective affinity group to achieve a selected goal, or in encouraging sub-populations of a population to promote their individual efforts so as to cause the collective efforts of each sub-population to match or exceed other sub-populations. These advantages are achieved in embodiments of the invention in which each individual uses a client device to enter values (either over a period of time, or in response to a prompt by the client device), and in which the aggregated or pooled information is presented by means of a broadcast medium or other communication technique. For example, members of a weight-loss club can aggregate their individual weight-loss each day, so that the aggregated results can be announced on a popular television show or displayed at their client devices.

SUMMARY OF THE INVENTION

The invention provides a method and system for aggregating and pooling information with feedback in a computer communication system. A communication system includes a server device and a set of client devices. Each client device collects information from an associated individual (whether by asking questions of those individuals, or accepting data input from peripheral devices), and transmits that data to a server device. The server device, or some other device at its behest, determines statistical information with regard to that data (such as aggregate, correlation, dispersion, or other measures), and provides that information to a communication channel for distribution to the individuals.

In a first preferred embodiment, the communication channel includes a broadcast communication channel that members of an affinity group can display. In a second preferred embodiment, the communication channel includes redistributing the determined statistical measures to associated individuals using the client devices. In a first aspect, the invention includes distributing the computed statistical measure (such as an aggregate or sum) for the entire population. For example, the first aspect would include announcing a total weight-loss for a weight-loss club on a television show. In a second aspect, the invention includes comparing the computed statistical measure for a first sub-population against a similar statistical measure for a second sub-population. For example, the second aspect would include comparing total weight-loss for selected teams and awarding a prize or other benefit to the team with the best result.

DETAILED DESCRIPTION OF THE PREFERRED EMBODIMENT

In the following description, a preferred embodiment of the invention is described with regard to preferred process steps and data structures. Embodiments of the invention can be implemented using general purpose processors or special purpose processors operating under program control, or other circuits, adapted to particular process steps and data structures described herein. Implementation of the process steps and data structures described herein would not require undue experimentation or further invention.

Related Applications

Inventions described herein can be used in combination or conjunction with inventions described in the following patent application(s):

Application Ser. No. 09/159,219, now abandoned, filed Sep. 23, 1998, in the name of Stephen J. Brown, titled "Modeling and Scoring Risk Assessment," assigned to the same assignee;

and

Application Ser. No. 09/159,058, now abandoned, filed Sep. 23, 1998, in the name of Stephen J. Brown, titled "Reducing Risk Using Behavioral and Financial Rewards," assigned to the same assignee.

These applications are hereby incorporated by reference as if fully set forth herein.

System Elements

Figure 1:
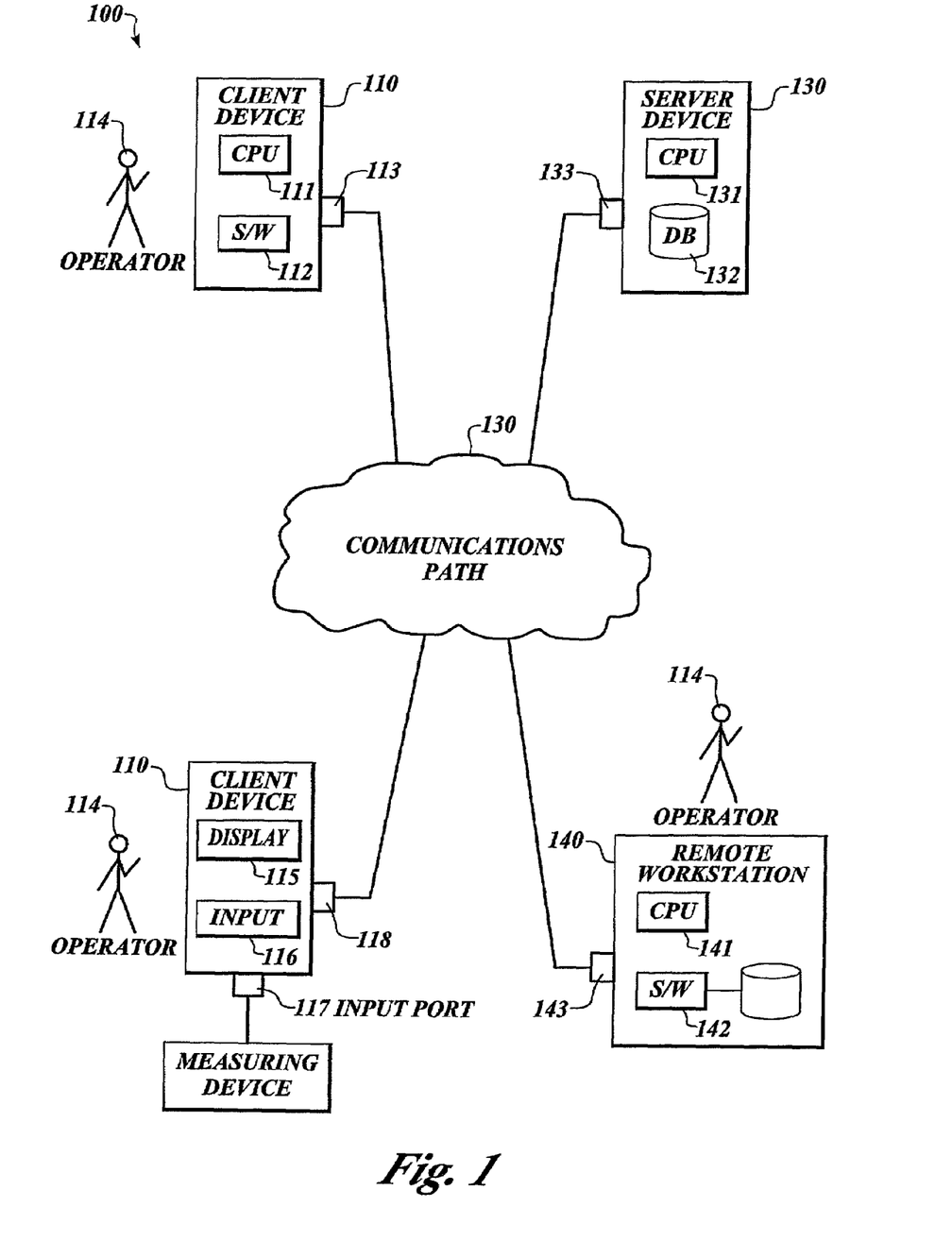
FIG. 1 shows a block diagram of a computer communication system for aggregating and pooling information.

FIG. 1 shows a block diagram of a computer communication system for aggregating and pooling information.

A system 100 includes a set of client devices 110, a communication path 120, a server device 130, and remote workstation 140.

Client Devices

The client devices 110 can be identical or can be of differing types. Thus, some client devices 110 can include the first type of client devices 110 as described below; some client devices 110 can include the second type of client devices 110 as described below, or some client devices 110 can include alternative types of client devices 110.

A first type of client device 110 includes a computer 111 (including a processor, memory, and mass storage), a set of web browser software 112, and a modem 113. An embodiment of the first client device 110 is described in detail in the On-Line Bidding Disclosures.

The first type of client device 110 operates under control of the web browser software 112 and operating software to allow an operator 114 to perform web browsing activity. Known web browser software is available from Netscape Corporation or from Microsoft Corporation. Web browsing activity is described in documentation available from either of those companies.

The first type of client device 110 uses the modem 113 to send and receive messages using the communication path 120. The communication path 120 is described in further detail below.

A second type of client device 110 includes a "remote apparatus" such as described in the following patent application:

U.S. Pat. No. 5,897,493, filed Apr. 30, 1997, in the name of Stephen J. Brown, titled "Monitoring System for Remotely Querying Individuals," assigned to the same assignee.

This patent is hereby incorporated by reference as if fully set forth herein.

The second type of client device 110 includes a display 115, an input device 116, an input port 117, and a communication interface 118.

The second type of client device 110 uses the display 115 to inform the operator 114 that input information is desired. The operator 114 can comprise a patient, a caregiver for the patient, or some other person. Preferably, the display 115 includes an alphanumeric display capable of displaying a question or request to the operator 114.

The second type of client device 110 uses the input device 116 to receive an answer to the question or request. For example, if the question asks for the patient's weight that day, the operator 114 uses the input device 116 to input the patient's weight for that day. The input device 116 can include a keypad or keyboard, such as for a computer or a television remote control, or can include a more restricted set of keys by which the operator 114 can increment, decrement, or accept a value to be entered for the patient's weight for that day.

The second type of client device 110 uses the input port 117 to receive data from a measuring device or other device. For example, the display 115 can request that the operator 114 couple the second client device 110 to a medical scale with an electronic readout, and the input port 117 can receive the electronic readout so as to directly receive a signal corresponding to the patient's weight for that day.

The second type of client device 110 uses the modem 113 similarly to the first type of client device 110, to send and receive messages using the communication path 120.

In alternative embodiments, the client device 110 may includes a wide variety of other devices, possibly including an electronic toy (such as a "game boy" or "virtual pet"), a telephone inter-operating with an interactive voice response system, a television set-top box inter-operating with a cable or satellite television interactive system, a medical device operated at medical personnel office, or any other system by which the operator 114 can enter a value to be used by the system 110 for aggregation and response.

Communication Path

The communication path 120 includes a set of electronic communication links for sending and receiving messages between the client devices 110 and the server device 130.

In a preferred embodiment, the communication path 120 includes the internet, to which the client devices 110 and the server device 130 are coupled. The messages are formatted using a communication protocol for use with the internet, such as TCP/IP, HTML, or a combination thereof. In alternative embodiments, the modem 113 may be replaced by any suitable communication interface, such as a direct communication link (such as a land-line or radio), another type of network link (such as a LAN, WAN, or combination thereof), or using another communication network (such as a private or public telephone network).

Server Device

The server device 130 includes a computer 131 (including a processor, memory, and mass storage), a database 132, and a modem 133. The server device 130 is similar to the "on-line auction company 12" described in detail in the On-Line Bidding Disclosures.

The server device 130 uses the modem 133 to send and receive messages using the communication path 120.

The server device 130 uses the database 132 to receive individual values entered by each client device 110, and to identify those individual values with their associated client device 110. The server device 130 also uses the database 132 to determine statistical measures of the pool of those values in response thereto.

In a preferred embodiment, the server device 130 operates in a similar manner as the "on-line auction company 12" described in detail in the On-Line Bidding Disclosures In a first preferred embodiment, the server device 130 aggregates the individual values entered by each client device 110. The server device 130 determines an aggregate value for the set of individual values, and sends that aggregate value back to each client device 110. Each client device 110 then displays the aggregate value to each individual operator 114, for use by the operator 114 or by an associated person, such as the patient.

For example, if the individual values each represent the weight lost by the patient for that day, the server device 130 can aggregate those values to determine a total weight lost by the entire set of patients having client devices 110. The server device 130 can then feed back that information to each client device 110 so that each patient can be motivated to contribute to the group effort, even if that individual patient's contribution is relatively minor.

The aggregate value determined by the server device 130 can be any statistical measure or other calculated measure responsive to the set of individual values provided by the set of client devices 110. For example, the aggregate value can be a total (as described with reference to the On-Line Bidding Disclosures), a maximum or minimum value, a median value, a selected centile value, a variance or standard deviation, or some other measure. It is expected that the aggregate value will have meaning to each individual patient associated with a client device 110, even if that individual patient's contribution to that aggregate is relatively minor.

In a second preferred embodiment, the server device 130 aggregates the individual values entered by each client device 110, but determines the aggregate values with regard to a set of affinity groups with which each individual is associated. As described in the On-Line Bidding Disclosures, each individual operator 114 at each individual client device 110 can choose to associate themselves with one or more selected affinity groups. As described in the On-Line Bidding Disclosures, these affinity groups contest against each other to obtain the "best" aggregate value. For example, in an on-line 13 auction, the best aggregate value is the highest total bid.

The server device 130 determines a separate aggregate value for each affinity group, and feeds back those separate aggregate values to each client device 110 (or to just those client devices 110 associated with the selected affinity group).

For example, if the individual values each represent the weight lost by the patient for that day, the server device 130 can determine separate aggregate values for each affinity group, to determine a total weight lost by the entire set of patients in each affinity group. The server device 130 can then feed back that information to each client device 110 so that each patient can be motivated to contribute to their selected affinity group effort, even if that individual patient's contribution is relatively minor.

The individual values and the separate aggregate values can be selected from a wide variety of possible values, so as to promote individual well being on behalf of each patient, and on the part of each selected affinity group.

For a first example, the individual values can be the measured height and weight for each patient, and the aggregate value (whether a single aggregate value or a set of separate aggregate values) can be a deviation from ideal weight for the entire affinity group.

For a second example, the individual values can be monetary contributions to a charitable or other financial cause, and the aggregate value (whether a single aggregate value or a set of separate aggregate values) can be a total monetary contribution.

For a third example, the individual values can be sales made by field salespersons for a company or product, and the aggregate value (whether a single aggregate value or a set of separate aggregate values) can be a total amount of sales.

Remote Workstation

A remote workstation 140 is coupled to the server device 130, so as to access information in the database 132 and to receive the aggregate values (whether a single aggregate value or a set of separate aggregate values).

The remote workstation 140, similar to the first type of client device 110, includes a computer 141 (including a processor, memory, and mass storage), a set of database software 142 or other display software (such as a set of web browser software), and a modem 143.

The remote workstation 140 uses the database software 142 or other display software to access the database 132. In accessing the database 132, the remote workstation 140 can receive the aggregate values (whether a single aggregate value or a set of separate aggregate values), or can receive selected sets of individual values from the client devices 110.

The remote workstation 140 uses the modem 143 similarly to the way the client device 110 or the server device 110 use their respective modems.

An operator 144 at the remote workstation 140 can use the database software 142 or other display software to add a broadcast message to the database 132. The server device 130, when feeding back the aggregate value, sends the broadcast message to the client devices 110.

The broadcast message can be a congratulatory message relating to the resultant aggregate value, an exhortatory or inspirational message for the one or more selected affinity groups, or a commercial or political message to one or more selected affinity groups.

For a first example, if the resultant aggregate value indicates that a weight-loss club has collectively lost 10,000 pounds of weight in one day, and this is a new record, the broadcast message can indicate the new record and congratulate all patients, even those whose contribution was relatively minor.

For a second example, the broadcast message can be a daily inspirational message for an affinity group, selected by the operator 144 at the remote workstation 140.

For a third example, the broadcast message can be a prize announcement (or an announcement of another benefit) to the individual patient who contributes most to the aggregate value. Similarly, when there are multiple affinity groups, the broadcast message can announce a prize or other benefit to the team with the best result.

Method of Operation

Figure 2:
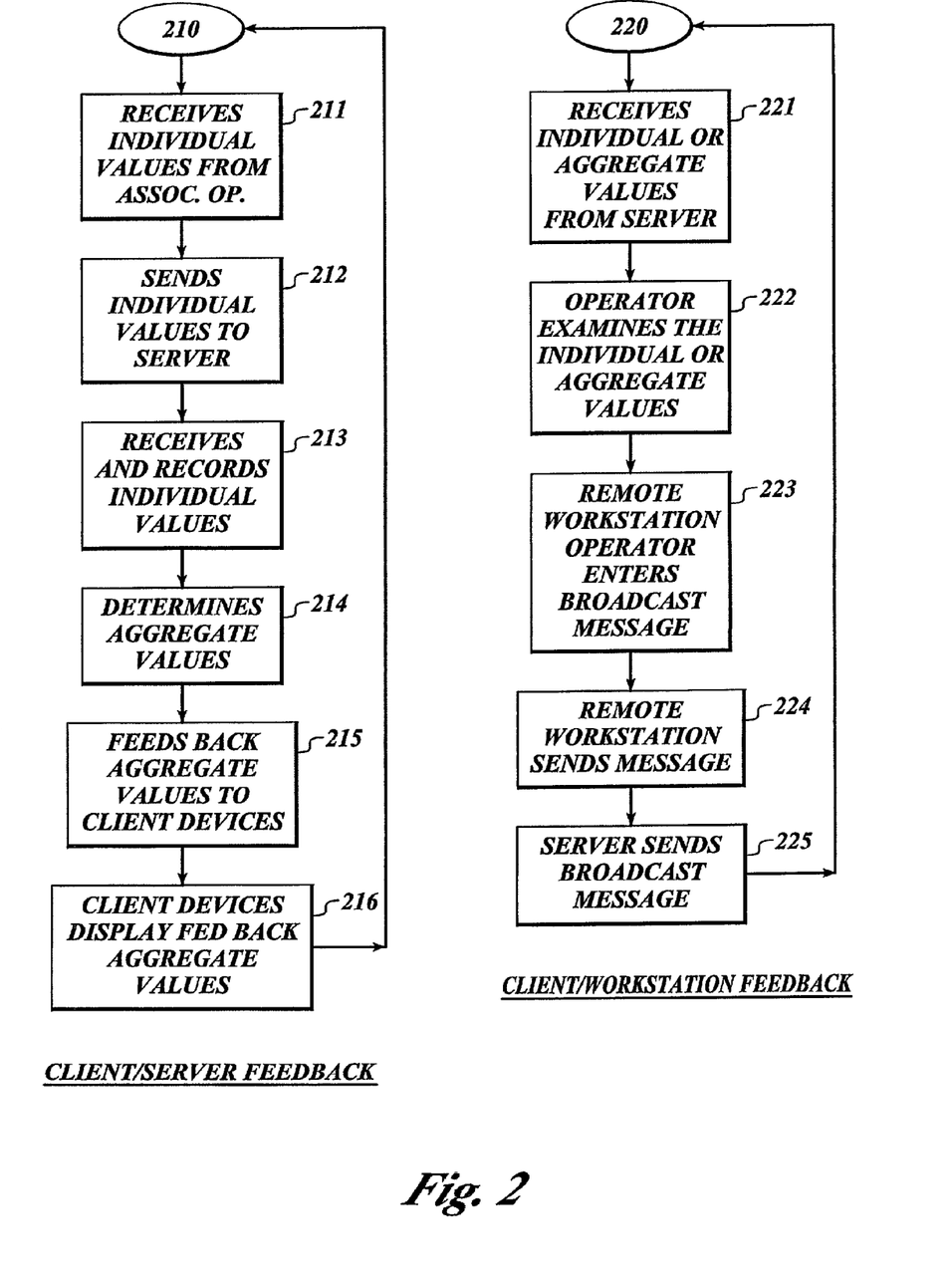
FIG. 2 shows a process flow diagram of a method for aggregating and pooling information in a computer communication system.

FIG. 2 shows a process flow diagram of a method for aggregating and pooling information in a computer communication system.

A method 200 includes a set of flow points to be reached, and steps to be performed, by elements of the system 100, including the client devices 110, the server device 130, and the remote workstation 140.

Client/Server Feedback

At a flow point 210, the system 100 is ready to receive individual values from client devices 110.

At a step 211, client devices 110 receive individual values from their associated operators 114. As noted above, each client device 110 can receive an individual value in response to a question-and-answer session, or can receive an individual value in response to a coupled data-collection device.

At a step 212, client devices 110 send their individual values to the server device 130. Operators at each client device 110 can select an affinity group in response to a menu of affinity groups presented by the server device 130.

At a step 213, the server device 130 receives the individual values and records them in the database 132.

At a step 214, the server device 130 determines one or more aggregate values (either a single aggregate value or a set of separate aggregate values) in response to the set of individual values.

At a step 215, the server device 130 feeds back the one or more aggregate values to the client devices 110.

At a step 216, the client devices 110 display the fed back aggregate values to their associated operators 114.

The method 200 thereafter proceeds with the flow point 210 again, such as a next day. For example, the method 200 can be selected to operate at a same or similar time each day.

Client/Workstation Feedback

At a flow point 220, the remote workstation 140 is ready to receive individual values or aggregate values from the server device 130.

At a step 221, the remote workstation 140 receives individual values or aggregate values from the server device 130.

At a step 222, the operator 144 at the remote workstation 140 examines the received individual values or aggregate values.

At a step 223, the operator 144 at the remote workstation 140 enters a broadcast message to be sent to client devices 110.

At a step 224, the remote workstation 140 sends the broadcast message to the server device 130.

At a step 225, the server device 130 sends the broadcast message to selected client devices 110 (or to all of them).

The method thereafter proceeds with the flow point 220 again, such as a next day. For example, the method 200 can be selected to operate at a same or similar time each day.

Alternative Embodiments

Although preferred embodiments are disclosed herein, many variations are possible which remain within the concept, scope, and spirit of the invention, and these variations would become clear to those skilled in the art after perusal of this application.

The invention claimed is:

1. A method of aggregating information from individuals in a population thereof, said method comprising
   a) coupling a client device to a data collection element for each of a plurality of individuals in the population, said data collection element including a weight scale;
   b) prompting each individual for health-related information, and collecting the health-related information for each individual at the client device associated with each individual, said health-related information including weight of each individual;
   c) sending the collected information from said client devices to a server device over a network;
   d) extracting the collected information from the data collection elements;
   e) generating statistical information from said collected information sent from a plurality of the client devices;
   f) distributing the statistical information to the individuals; and
   g) repeating steps a-d after a period of time has elapsed;
   wherein said statistical information comprises a first statistical measure for a first subpopulation of individuals within the plurality of individuals and a second statistical measure for a second subpopulation of individuals within the plurality of individuals, said first statistical measure based upon weight of said first subpopulation of individuals and said second statistical measure based upon weight of said second subpopulation of individuals;
   h) comparing the first statistical measure with the second statistical measure, and distributing a result of the comparison to the first subpopulation of individuals and to the second subpopulation of individuals: and
   i) awarding a benefit to said first subpopulation or said second subpopulation based on the result of the comparison.

2. The method of claim 1, wherein the statistical information is distributed by the server device to the client devices.

3. The method of claim 1, wherein said first statistical measure is based upon a total weight loss for said first subpopulation and said second statistical measure is based upon a total weight loss for said second subpopulation.

4. A system for aggregating information for individuals in a population thereof said system including:
   a data collection element disposed for collecting an individual value comprising health-related information for each of plurality of individuals in the population in response to a prompt received by the client device for the health-related information, said data collection element including a weight scale;
   a server device, disposed for receiving said individual values, for determining at least one aggregate value in response thereto, and extracting the collected information from the data collection elements over a network, the collected information including weight of each individual;
   wherein said server device distributes said at least one aggregate value to a plurality of client devices;
   wherein each of the client devices repeats collecting the individual value for the individual associated therewith, said server device repeats the determination of at least one aggregate value in response to the repeated collection performed by the client devices and said server device distributes the repeated determination of the at least one aggregate value to a plurality of said client devices, when a preset period of time has elapsed since the previous collection of individual values, determination of at least one aggregate value and distribution of said at least one aggregate value; and
   wherein the at least one aggregate value comprises a first statistical measure for a first subpopulation of individuals within the plurality of individuals and a second statistical measure for a second subpopulation of individuals within the plurality of individuals, said first statistical measure based upon weight of said first subpopulation of individuals and said second statistical measure based upon weight of said second subpopulation of individuals;
   wherein the server device is configured to compare the first statistical measure with the second statistical measure, and distribute a result of the comparison to the first subpopulation of individuals and to the second subpopulation of individuals; and
   wherein the server device is further configured to award a benefit to said first subpopulation or said second subpopulation based on the result of the comparison.

5. The system of claim 4, further comprising a set of client devices, each coupled to a respective data collection element.

6. The system of claim 5, further comprising a communication path between said client devices and said server device.

7. The system of claim 4, wherein said first statistical measure is based upon a total weight loss for said first subpopulation and said second statistical measure is based upon a total weight loss for said second subpopulation.

8. A method of aggregating information from individuals in a population thereof, said method comprising:
   a) coupling a client device a data collection element for to each of a plurality of individuals in the population said data collection element including a weight scale;
   b) prompting each individual for health-related information, and collecting the health-related information for each individual at the client device associated with each individual, said health-related information including weight of each individual;
   c) sending the collected information from said client devices to a server device over a network;
   d) extracting the collected information;
   e) generating statistical information from said collected information sent from a plurality of the client devices;
   f) distributing the statistical information to the individuals; and
   g) repeating steps a-d after a period of time has elapsed;
   wherein said statistical information comprises a first statistical measure for a first subpopulation of individuals within the plurality of individuals and a second statistical measure for a second subpopulation of individuals within the plurality of individuals, said first statistical measure based upon weight of said first subpopulation of individuals and said second statistical measure based upon weight of said second subpopulation of individuals;
   i) comparing the first statistical measure with the second statistical measure, and distributing a result of the comparison to the first subpopulation of individuals and to the second subpopulation of individuals; and
   j) awarding a benefit to said first subpopulation or said second subpopulation based on the result of the comparison.

9. The method of claim 8, wherein the statistical information is distributed by the server device to the client devices.

10. The method of claim 8, wherein said first statistical measure is based upon a total weight loss for said first subpopulation and said second statistical measure is based upon a total weight loss for said second subpopulation.

11. A system for aggregating information for individuals in a population thereof, said system including:
   a client device a data collection element disposed for collecting an individual value comprising health-related information for each of plurality of individuals in the population in response to a prompt received by the client device for the health-related information, said data collection;

a server device, disposed for receiving said individual values, for determining at least one aggregate value in response thereto, extracting the collected information from the data collection elements over a network, the collected information including weight of each individual; and wherein said server device distributes said at least one aggregate value to a plurality of said client devices over a network;

wherein each of the client devices repeats collecting the individual value for the individual associated therewith, said server device repeats the determination of at least one aggregate value in response to the repeated collection performed by the client devices and said server device distributes the repeated determination of the at least one aggregate value to a plurality of said client devices, when a preset period of time has elapsed since the previous collection of individual values, determination of at least one aggregate value and distribution of said at least one aggregate value;

wherein the at least one aggregate value comprises a first statistical measure for a first subpopulation of individuals within the plurality of individuals and a second statistical measure for a second subpopulation of individuals within the plurality of individuals, said first statistical measure based upon weight of said first subpopulation of individuals and said second statistical measure based upon weight of said second subpopulation of individuals;

wherein the server device is configured to compare the first statistical measure with the second statistical measure, and distribute a result of the comparison to the first subpopulation of individuals and to the second subpopulation of individuals; and wherein the server device is further configured to award a benefit to said first subpopulation or said second subpopulation based on the result of the comparison.

12. The system of claim 11, further comprising a communication path between said client devices and said server device.

13. The system of claim 11, wherein said first statistical measure is based upon a total weight loss for said first subpopulation and said second statistical measure is based upon a total weight loss for said second subpopulation.

* * * * *